United States Patent [19]

Port et al.

[11] 4,379,142

[45] Apr. 5, 1983

[54] THROMBIN INHIBITOR AND PREPARATION AND USE THEREOF

[75] Inventors: Hans Port, Weilheim-Unterhausen; Jürgen Schrenk, Weilheim; Peter Wunderwald, Haunshofen, all of Fed. Rep. of Germany

[73] Assignee: Boehringer Mannheim GmbH, Mannheim-Waldhof, Fed. Rep. of Germany

[21] Appl. No.: 309,665

[22] Filed: Oct. 8, 1981

[30] Foreign Application Priority Data

Oct. 9, 1980 [DE] Fed. Rep. of Germany ....... 3038163

[51] Int. Cl.³ .............................................. A23J 1/06
[52] U.S. Cl. .................................... 424/101; 424/177; 260/112 B
[58] Field of Search .................... 260/112 B; 424/101, 424/177

[56] References Cited

U.S. PATENT DOCUMENTS 4,087,415  5/1978  Bick ................................ 260/112 B

OTHER PUBLICATIONS

Chem. Abs. 81: 88767m, 1974.
Rosenberg, R. D., J. Biol. Chem., vol. 248, No. 18, pp. 6490–6505, 1973.
Briginshaw, G. F. et al., Thrombosis Res., vol. 4, pp. 463–477, 1974.
Briginshaw, G. F. et al., Archives of Biochemistry and Biophysics, vol. 161, pp. 683–690, 1974.

Primary Examiner—Allan Lieberman
Assistant Examiner—Patricia Short
Attorney, Agent, or Firm—Felfe & Lynch

[57] ABSTRACT

Thrombin inhibitor comprising a glycoprotein of a molecular weight of 68,000 to 69,000 Dalton and an isoelectric point of pH 4.5, and is further characterized in that it inhibits thrombin in the presence of dextran sulfate at least twice as strongly as in the presence of heparin, differs immunologically from antithrombin III, and does not inhibit factor Xa, plasmin and trypsin.

6 Claims, No Drawings

THROMBIN INHIBITOR AND PREPARATION AND USE THEREOF

This invention relates to a new thrombin inhibitor. In addition the invention relates to the preparation of this inhibitor and with methods of using the same pharmaceutically.

The proteolytic enzyme thrombin plays an important part in the blood coagulation system. It is known that, in the coagulation system, a specific inactivator for thrombin is present which, in the presence of heparin, is able to inhibit thrombin and which is called antithrombin III. Therefore, the use of heparin as an anti-coagulant plays an important part in therapy and research. In addition, antithrombin III (AT III) is an important component of test systems for the coagulation properties of serum. However, AT III also inhibits thrombin in the absence of heparin in a time-dependent reaction and, apart from thrombin, also inhibits trypsin, plasmin and Factor Xa and thus is relatively non-specific.

Surprisingly, we have now found a new, specific thrombin inhibitor which differs from AT III in many respects.

The thrombin inhibitor according to the present invention inhibits thrombin in the presence of dextran sulphate at least twice as strongly as in the presence of heparin, differs immunologically from antithrombin III, does not inhibit factor Xa, plasmin and trypsin, is a glyco-protein, has a molecular weight of 68,000 to 69,000 Dalton and has an isoelectric point at pH 4.5.

Since the new thrombin inhibitor binds less strongly to heparin than AT III, in the following it is referred to as AT-BM (antithrombin binding moderately to heparin).

AT-BM does not react with AT III antiserum so that the two antithrombins do not display an immunological cross reaction. Whereas AT III requires, for an optimum thrombin inhibition, only a heparin concentration of the order of 0.02 USP/ml., in the case of AT-BM, the heparin concentration needed for the optimum thrombin inhibition is more than 1.0 USP/ml.

Whereas human AT III also inhibits, inter alia, Factor Xa, plasmin and trypsin and reacts with human thrombin insubstantially more strongly than with bovine thrombin, the new human AT-BM is almost completely thrombin-specific and inhibits human thrombin markedly more strongly than bovine thrombin. Furthermore, the thrombin inhibition by AT III is more strongly promoted by heparin than by other activators, such as dextran sulphate. On the other hand, in the case of AT-BM with dextran sulphate, a thrombin inhibition is achieved which is two to three times stronger than in the presence of heparin.

Whereas AT III inhibits thrombin in a time-dependent reaction even in the complete absence of co-factors, such as heparin, under these conditions AT-BM displays no inhibiting action.

Because of the above properties, the new thrombin inhibitor AT-BM according to the present invention can be used similarly to AT III in therapeutic and diagnostic processes and, in addition, is of interest for research.

The differences of specificity of AT-BM in comparison with AT III in the presence of different amounts of heparin are shown in the following Table 1:

TABLE 1

| | Specificity comparison AT-BM/AT III | | | |
|---|---|---|---|---|
| | AT III (U/ml.) with | | AT-BM (U/ml.) with | |
| | 0.02 | 1.75 | 0.02 | 1.75 |
| | USP heparin/ml. | | USP heparin/ml. | |
| protease | test vol. | | test vol. | |
| bovine thrombin | | | | |
| total | 22.5 | 24.4 | 6.6 | 29.0 |
| "α-thrombin" | 25.9 | 25.6 | 3.7 | 40.3 |
| "β-thrombin" | 20.0 | 23.5 | 0.4 | 4.5 |
| human thrombin | | | | |
| total | 29.4 | 30.8 | 8.4 | 74.0 |
| "α-thrombin" | 23.0 | 31.7 | 6.2 | 101.1 |
| "β-thrombin" | 29.0 | 37.7 | 0.1 | 18.9 |
| Factor Xa | 5.6 | 29.5 | 0 | 0 |
| plasmin | 0 | 14.5 | 0 | 0.4 |
| trypsin | 23.5 | 16.5 | 0 | 0 |

In normal human plasma, the new AT-BM is present together with AT III and provides, on average, about 20% of the total antithrombin activity, the remaining approximately 80% being due to the AT III. Under certain circumstances, the ratio of AT-BM to AT III can be changed, this being shown by the experimental results summarised in the following Table 2:

TABLE 2

Antithrombin determination with bovine thrombin and 1.75 U/ml. heparin at 25° C.

| plasma | n | ∅ total AT U/ml. | % total AT AT-BM | % total AT AT-III |
|---|---|---|---|---|
| normal | 5 | 8.4 ± 0.3 | 20.8 ± 5.4 | 79.2 ± 5.4 |
| pregnant | 3 | 7.5 ± 2.5 | 14.0 ± 2.4 | 86.0 ± 2.4 |
| children | 6 | 6.1 ± 0.4 | 15.5 ± 0.5 | 84.5 ± 0.5 |
| marcumar | 8 | 5.7 ± 1.4 | 11.4 ± 4.5 | 88.5 ± 3.9 |
| suspected hepatitis | 3 | 4.6 ± 1.9 | 10.0 ± 5.6 | 90.0 ± 5.6 |
| serum | 3 | 3.9 ± 0.7 | 32.0 ± 4.4 | 68.0 ± 4.4 |

As already mentioned, the co-factor specificity of the new AT-BM is different from that of AT III. In particular, in the case of AT III, the highest inhibiting capacity is achieved in the presence of heparin, whereas in the case of AT-BM even substantially higher inhibiting values can be achieved with dextran sulphate. The values determined are given in the following Table 3:

TABLE 3

Comparison of the co-factor specificity of AT III/AT-BM in the case of inhibition of bovine thrombin

| co-factor | anti-thrombin activity U/ml. of | |
|---|---|---|
| (25 μg./ml.) | AT III | AT-BM |
| heparin (15 μg./ml. = 1.75 USP/ml.) | 27.5 | 13.2 |
| λ-carrageenan | 5.4 | 9.3 |
| xylan | 6.3 | 1.2 |
| sodium dextran sulphate (M.W. 500,000) | 4.1 | 33.0 |
| polystyrene sulphonate | 0 | 0 |

AT-BM also differs considerably in its properties from other known protease inhibitors present in plasma. This can readily be seen from the following Table 4:

TABLE 4

Comparison of AT-BM with known protease inhibitors in human plasma

| inhibitor | | M.W. in KD (1) | binding to heparin seph. | Immunol. cross-reaction with AT-BM | inhibition of | | | | |
|---|---|---|---|---|---|---|---|---|---|
| | | | | | thrombin | Factor Xa | plasmin | trypsin | chymotrypsin |
| α-1-antitrypsin | | 54 | — | — | + | | + | + | + |
| α-1-antichymotrypsin | | 68 | — | — | | | | | + |
| inter-α-trypsin inhibitor | } CRM² | 140 | + | — | + | | + | ± | ± |
| acid-stable proteinase inhibitor | | 34 | | | | | | | |
| α₂-macroglobulin | | 725 | — | — | + | | + | + | + |
| α₂-antiplasmin | | 70 | — | | | | + | + | |
| antithrombin III | | 67 | ++ | — | ++ | ++ | + | + | |
| C 1-esterase inactivator I | } CRM² | 105 | | | | | + | — | |
| C 1-esterase inactivator II | | 96 | ± | — | | | + | — | |
| antithrombin-BM | | 68–69 | + | not applicable | ++ | — | — | — | — |

(1) KD = Kilodalton
²CRM = immunologically cross-reacting with one another.

The thrombin inhibitor AT-BM according to the present invention can be obtained on the basis of its differing properties in comparison with AT III, for example with regard to heparin, by treating a solution containing the inhibitor with carrier-bound insoluble co-factor, AT III and AT-BM thereby being bound to the co-factor and the AT-BM, because of its differing affinity to the co-factor in comparison with AT III, is separated from the latter. As co-factor, there can be used not only heparin but also heparin-analogous compounds, for example dextran sulphate.

Therefore, the process according to the present invention for obtaining the thrombin inhibitor AT-BM is characterised in that serum, plasma or a fraction obtained therefrom is treated with insoluble, carrier-bound heparin or dextran sulphate, the latter, after the removal of non-bound material, is eluted with an ion strength of 0.12 to 0.36 and a pH value of from 6.5 to 8.3 and the AT-BM recovered from the eluate. Under these conditions, the AT III is not eluted.

For the adjustment of the pH value range, use can be made of buffer substances which buffer in the desired range. The concentration of the buffer is preferably from about 0.005 to 0.1 M. The best results are obtained at pH values of from 7.5 to 8.0. The buffer used is preferably phosphate or tris buffer.

As already mentioned, the process according to the present invention can be carried out directly on serum or plasma. Preferably, however, a pre-purification is carried out in known manner. A plasma fraction obtained by adsorption on aluminium hydroxide gel, ammonium sulphate fractionation and dialysis has proved to be especially suitable. An appropriate method of pre-purification is described, for example, in J.A.C.S., 68, 459–475/1946). In particular, the there-described Fraction IV is a suitable starting material which can be obtained without great expense.

The purification is preferably carried out in the presence of a sequestering agent, for example ethylenediamine-tetraacetic acid (EDTA), the concentration of which is preferably from 5 to 20 mM.

The present invention also provides a pharmaceutical composition which contains the new thrombin inhibitor according to the present invention, in admixture with conventional pharmaceutical additives and diluents.

The following Example is given for the purpose of illustrating the present invention:

EXAMPLE 1 kg. of Fracton IV (obtained in the manner described in J.A.C.S., 68, 459–475/1946) is homogenised in 20 liters of 0.01 M tris buffer, 0.01 M EDTA and 0.01 M sodium chloride (pH 8) and centrifuged. The opalescent supernatant is mixed with about 15 volume % aluminium hydroxide gel, stirred for 30 minutes and centrifuged off.

The gel precipitate is washed out with the above-described buffer and eluted with 1.5 times the gel volume of 0.2 M phosphate buffer (pH 7.8). The eluate is adjusted with solid ammonium sulphate to 1.4 mol/liter and the precipitate is centrifuged off. The supernatant is slowly brought to 3 M ammonium sulphate and again centrifuged. The precipitate is taken up as concentrated as possible with 0.01 M phosphate buffer (pH 7.8) and dialysed against the same buffer.

The dialysate is chromatographed over heparin-"Sepharose". Thereafter, it is washed with 2 column volumes of 0.01 M phosphate buffer (pH 7.8) and then eluted with a salt gradient of 0 to 1.5 M sodium chloride in 0.01 M phosphate buffer (pH 7.8), the AT-BM being eluted at 0.1 to 0.3 M sodium chloride. The eluate is precipitated with 2.8 to 3.2 M ammonium sulphate and taken up in the smallest possible volume of 0.01 M tris buffer +0.01 M EDTA +0.01 M sodium chloride (pH 8.0). After dialysis against the same buffer, the preparation is lyophilised.

It will be understood that the specification and examples are illustrative but not limitative of the present invention and that other embodiments within the spirit and scope of the invention will suggest themselves to those skilled in the art.

What is claimed is:

1. Thrombin inhibitor comprising a glycoprotein of a molecular weight of 68,000 to 69,000 Dalton and an isoelectric point of pH 4.5, obtained by the process of treating plasma, serum or a fraction obtained therefrom with an insoluble carrier-bound heparin or dextran sulfate, eluting the latter, after removal of non-bound material, with a salt solution having an ion strength of 0.12 to 0.36 and a pH value from 6.5 to 8.3, and recovering the thrombin inhibitor from the eluate, and is further characterized in that it inhibits thrombin in the presence of heparin, differs immunologically from antithrombin III, and does not inhibit factor Xa, plasmin and trypsin.

2. Process for obtaining a thrombin inhibitor comprising a glycoprotein of a molecular weight of 68,000 to 69,000 Dalton and an isoelectric point of pH 4.5, and characterized in that it inhibits thrombin in the presence of dextran sulfate at least twice as strongly as in the presence of heparin, differs immunologically from anti-thrombin III, and does not inhibit factor Xa, plasmin and trypsin which process comprises the steps of treating plasma, serum or a fraction obtained therefrom with an insoluble carrier-bound heparin or dextran sulfate, eluting the latter, after removal of non-bound material, with a salt solution having an ion strength of 0.12 to 0.36 and a pH value from 6.5 to 8.3, and recovering the thrombin inhibitor from the eluate.

3. Process as claimed in claim 2, wherein the plasma fraction is pre-purified by adsorption of aluminium hydroxide gel, ammonium sulphate fractionation and dialysis.

4. A thrombin inhibitor prepared by the process of claim 2.

5. A thrombin inhibitor prepared by the process of claim 3.

6. A pharmaceutical composition comprising, in admixture with a pharmaceutical carrier, an effective amount of a thrombin inhibitor as claimed in claim 1.

* * * * *